US009724039B2

(12) United States Patent
Xia et al.

(10) Patent No.: US 9,724,039 B2
(45) Date of Patent: Aug. 8, 2017

(54) APPARATUS, SYSTEM, AND METHOD RECORDING ANATOMIC ORIENTATION AND POSITION

(71) Applicants: James J. Xia, Houston, TX (US); Jaime Gateno, Bellaire, TX (US)

(72) Inventors: James J. Xia, Houston, TX (US); Jaime Gateno, Bellaire, TX (US)

(73) Assignee: THE METHODIST HOSPITAL, Houston, TX (US)

( * ) Notice: Subject to any disclaimer, the term of this patent is extended or adjusted under 35 U.S.C. 154(b) by 124 days.

(21) Appl. No.: 14/335,644

(22) Filed: Jul. 18, 2014

(65) Prior Publication Data

US 2014/0330169 A1   Nov. 6, 2014

Related U.S. Application Data

(63) Continuation of application No. 12/682,724, filed as application No. PCT/US2008/080629 on Oct. 21, 2008, now Pat. No. 8,795,206.

(60) Provisional application No. 60/981,654, filed on Oct. 22, 2007.

(51) Int. Cl.
*A61B 5/00* (2006.01)
*A61B 5/11* (2006.01)

(52) U.S. Cl.
CPC ......... *A61B 5/4887* (2013.01); *A61B 5/1114* (2013.01); *A61B 5/1127* (2013.01); *A61B 5/4504* (2013.01); *A61B 5/6814* (2013.01); *A61B 2505/05* (2013.01)

(58) Field of Classification Search
CPC ....... A61B 5/11; A61B 5/1111; A61B 5/6814; A61B 5/68; A61B 5/682; A61B 5/1114; A61B 5/1127; A61B 5/4504; A61B 5/4887; A61B 2505/05
See application file for complete search history.

(56) References Cited

U.S. PATENT DOCUMENTS

| | | | |
|---|---|---|---|
| 5,343,391 A | 8/1994 | Mushabac |
| 5,951,498 A | 9/1999 | Arnett |
| 6,096,048 A | 8/2000 | Howard, III et al. |
| 6,120,290 A | 9/2000 | Fukushima et al. |
| 6,259,942 B1 | 7/2001 | Westermann et al. |
| 6,381,485 B1 | 4/2002 | Hunter et al. |
| 6,786,877 B2 | 9/2004 | Foxlin |
| 6,888,546 B1 | 5/2005 | Kim |
| 7,182,737 B2 | 2/2007 | Kim et al. |
| 8,029,277 B2 | 10/2011 | Imgrund et al. |
| 8,078,255 B2 | 12/2011 | Bhandarkar et al. |
| 8,113,829 B2 | 2/2012 | Sachdeva et al. |
| 8,337,202 B2 | 12/2012 | Bando et al. |
| 8,382,686 B2 | 2/2013 | Guman et al. |

OTHER PUBLICATIONS

International Searching Authority (United States), Authorized Officer Lee W. Young, International Search Report, for Application No. PCT/US2008/080629, mailed Feb. 13, 2009, 2 pages, Alexandria, VA.

(Continued)

*Primary Examiner* — Max Hindenburg
(74) *Attorney, Agent, or Firm* — Haynes & Boone, LLP

(57) ABSTRACT

Disclosed are systems, apparatuses and methods for recording images of one or more selected anatomical features, and to facilitate re-orientation and/or re-positioning of such images to one or more desired positions.

10 Claims, 15 Drawing Sheets

(56) References Cited

OTHER PUBLICATIONS

International Searching Authority (United States), PCT Written Opinion of the International Searching Authority, Authorized Officer Lee W. Young, for Application No. PCT/US2008/080629, mailed Feb. 13, 2009, 6 page, Geneva Switzerland.
The International Bureau of WIPO, PCT International Preliminary Report on Patentability, Authorized Officer Yolaine Cussac, , for Application No. PCT/US2008/080629, mailed Apr. 27, 2010, 7 pages, Geneva Switzerland.
U.S. Patent & Trademark Office, non-Final Office Action, for U.S. Appl. No. 12/682,724, mailed Mar. 19, 2013, 8 pages, Alexandria, VA.
U.S. Patent & Trademark Office, Final Office Action, for U.S. Appl. No. 12/682,724, mailed Nov. 25, 2013, 7 pages, Alexandria, VA.

FIG. 3

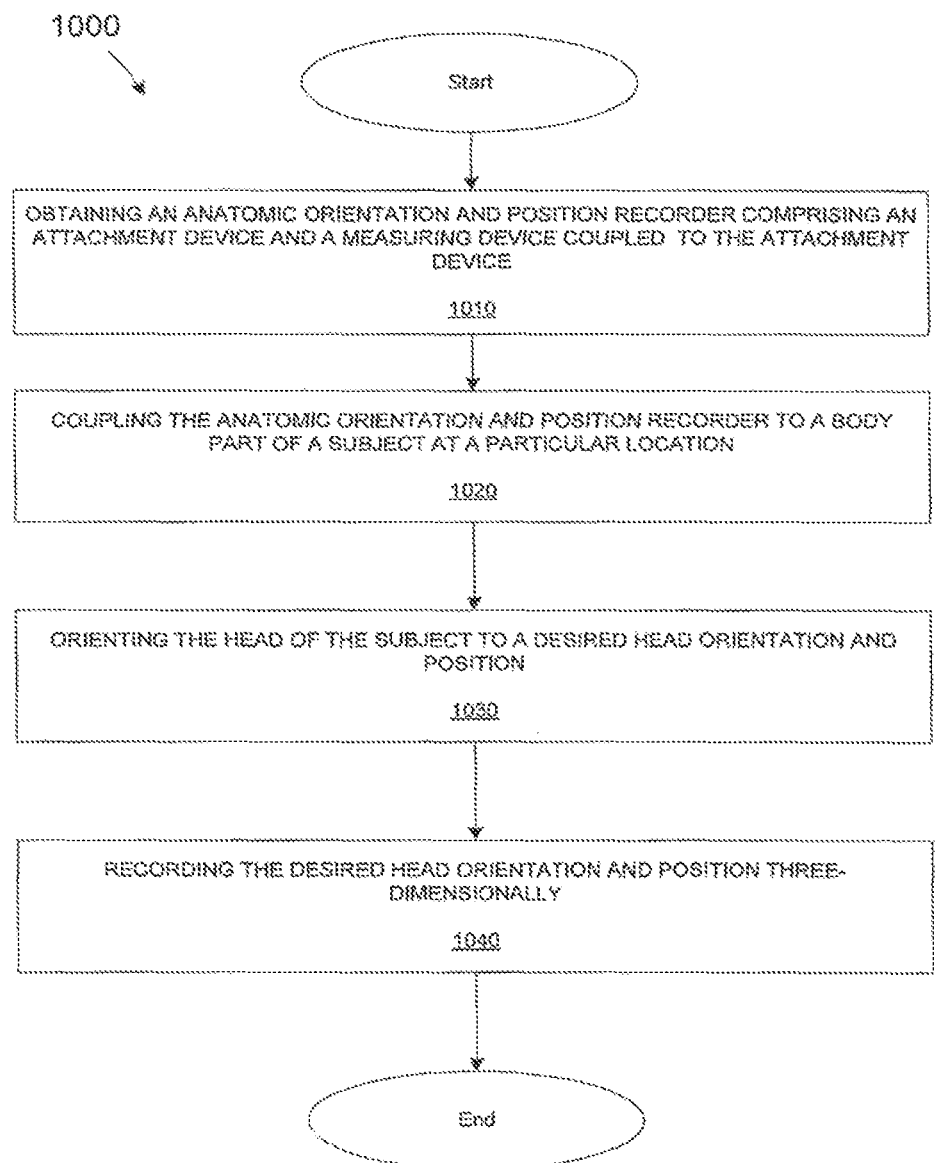

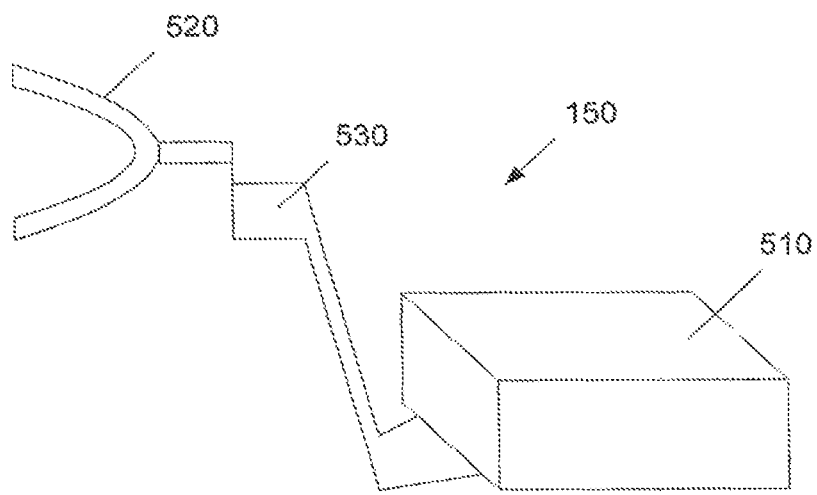
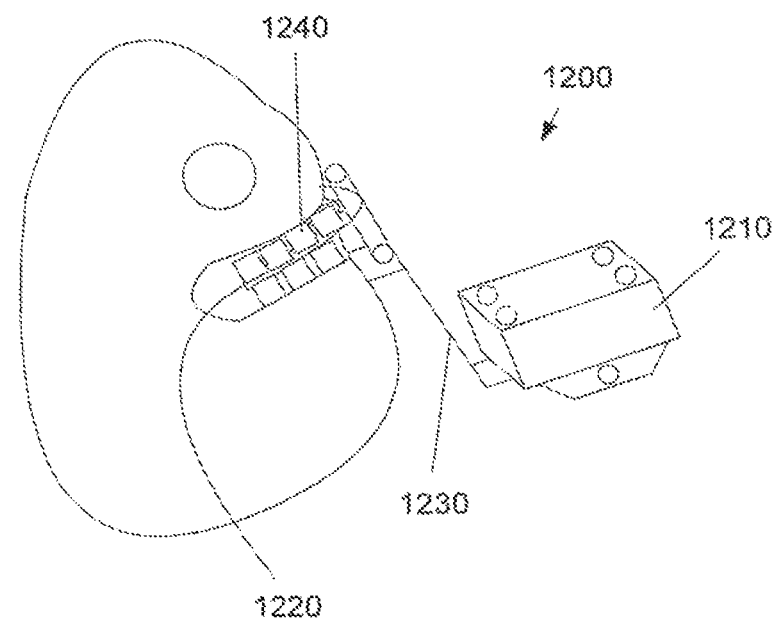

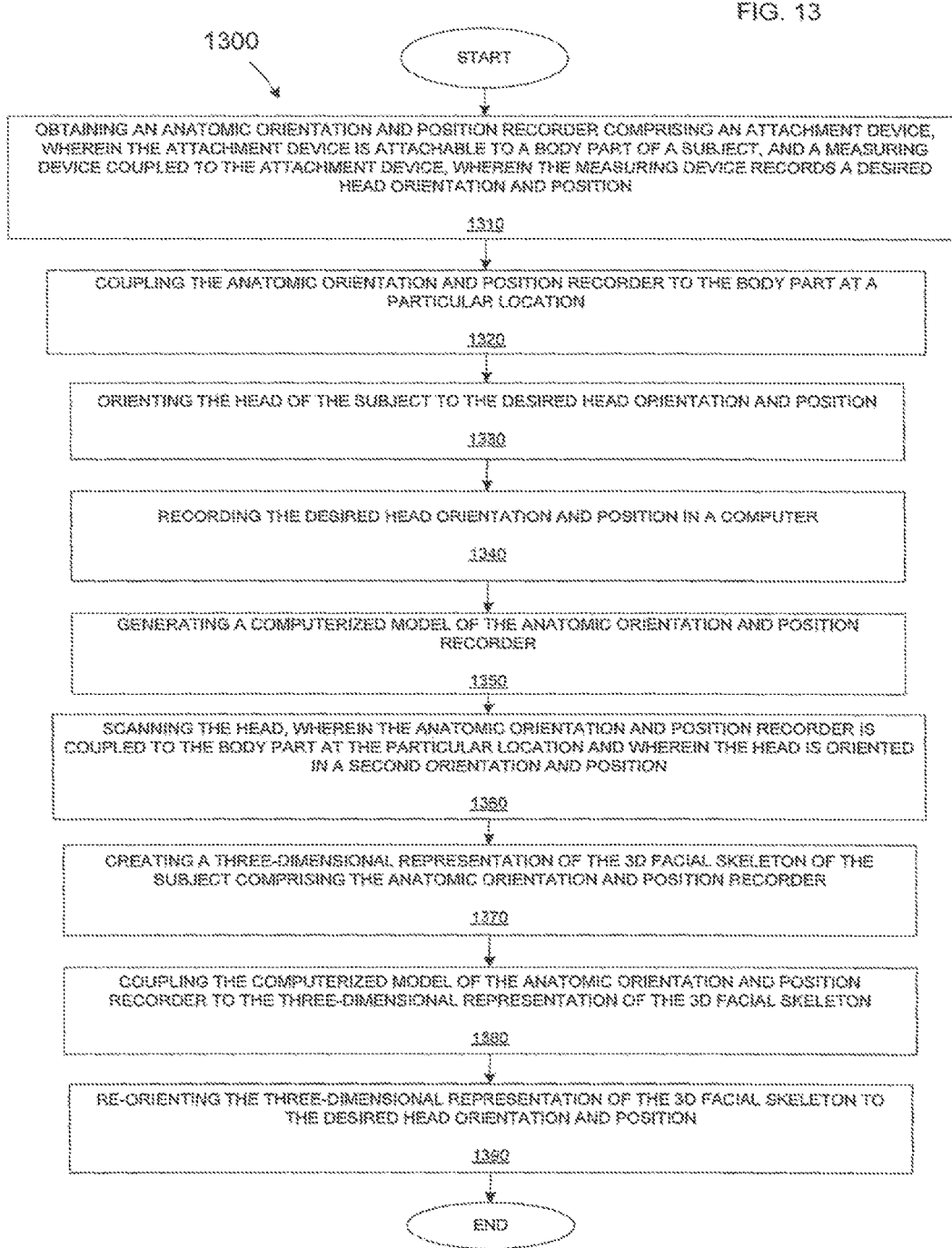

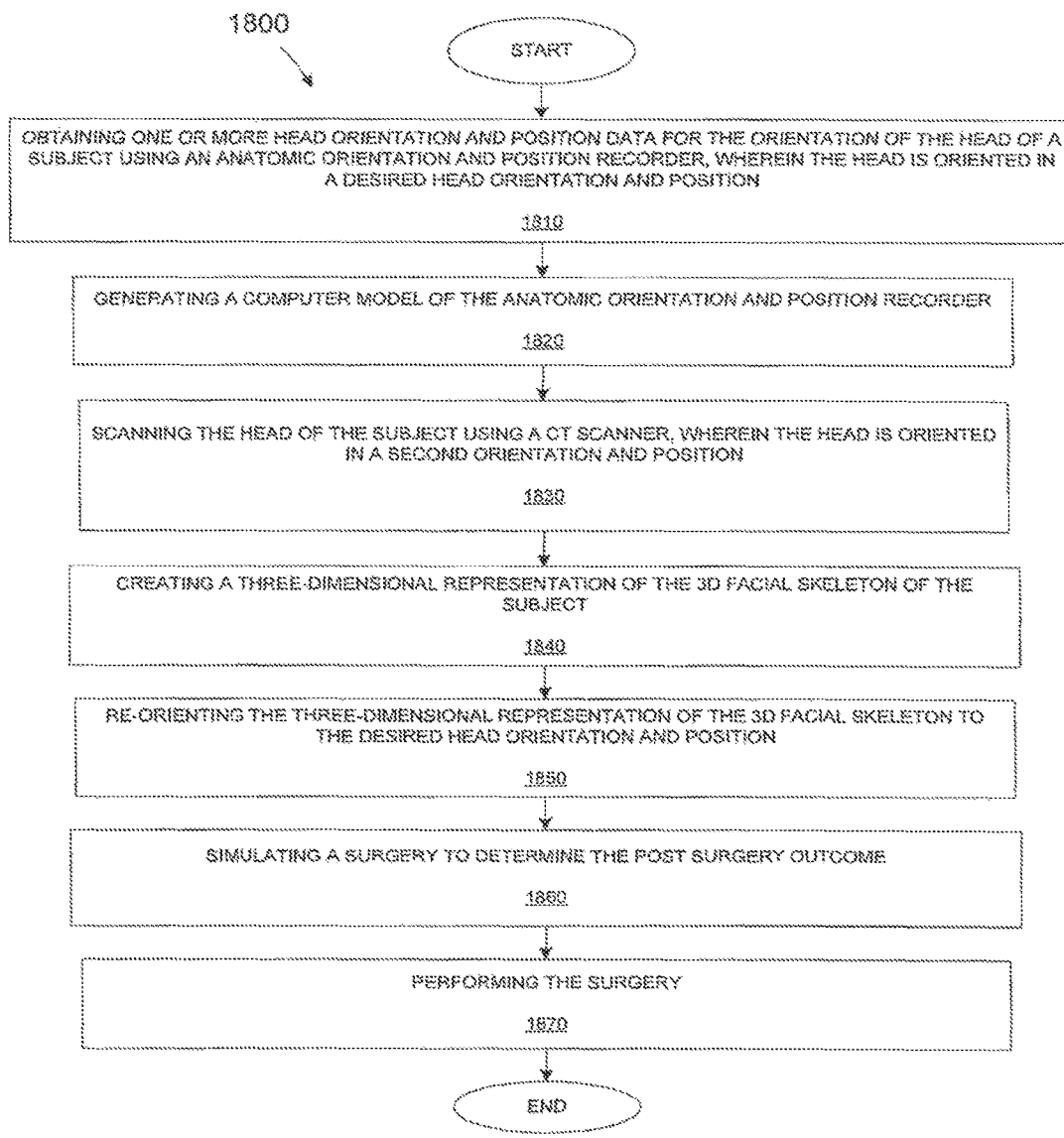

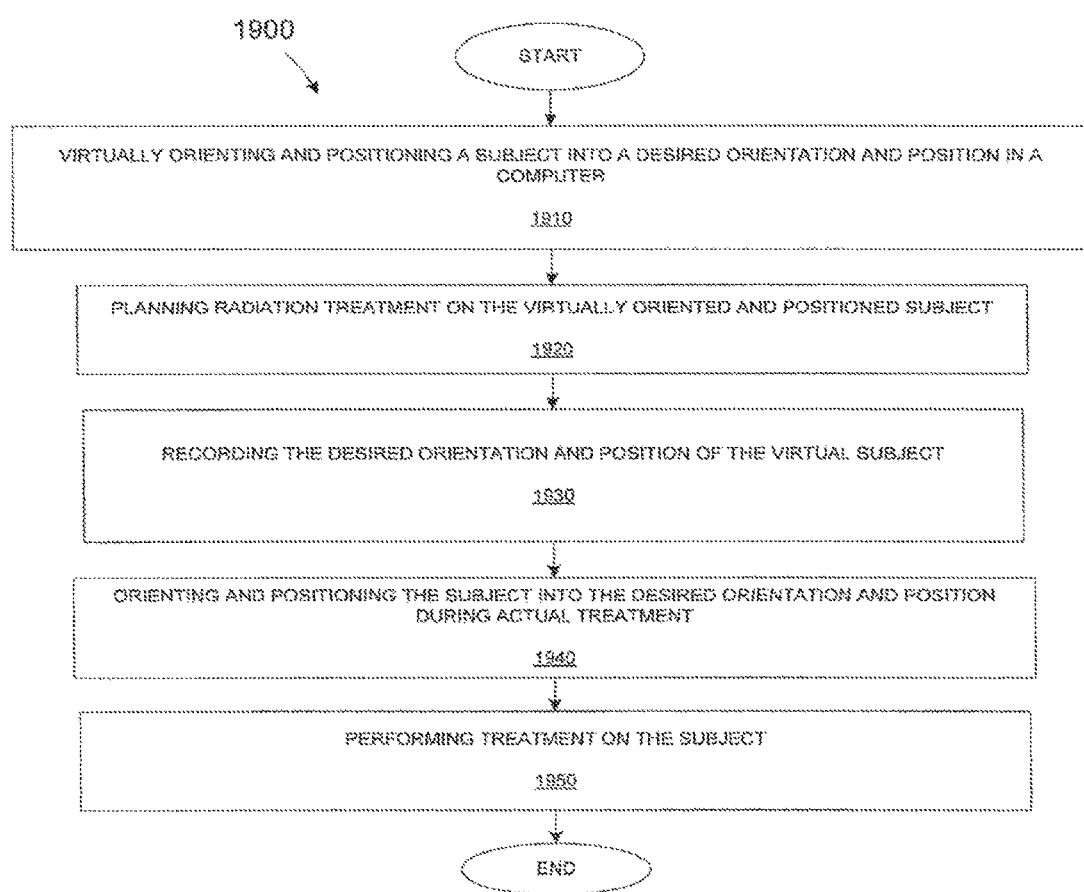

APPARATUS, SYSTEM, AND METHOD RECORDING ANATOMIC ORIENTATION AND POSITION

CROSS-REFERENCE TO RELATED APPLICATIONS

The present application is a continuation of U.S. patent application Ser. No. 12/682,724, filed Apr. 19, 2010 (effective filing date Jul. 19, 2010; now allowed); which was a U.S. §371 nationalization of PCT Intl. Pat. Appl. No. PCT/US08/80629, filed Oct. 21, 2008 (nationalized); which claims benefit of U.S. Prov. Pat. Appl. No. 60/981,654, filed Oct. 22, 2007; the contents of each of which is specifically incorporated herein in its entirety by express reference thereto.

BACKGROUND OF THE INVENTION

Statement Regarding Federally Sponsored Research or Development

Not Applicable.

NAMES OF THE PARTIES TO A JOINT RESEARCH AGREEMENT

Not Applicable.

FIELD OF THE INVENTION

The present invention relates generally to the fields of medical imaging and surgery, and in particular, relates to positioning and reorientation of medical imaging data, and particularly to a system, apparatus and method for recording an anatomic orientation and position of one or more selected anatomical features.

SUMMARY OF THE INVENTION

In a first embodiment, the invention provides a system for determining the orientation of a selected anatomical feature of the body of an animal. In an overall and general sense, the system comprises: a processor; (a) a database for storing a plurality of data, wherein the plurality of data comprises three-dimensional data for determining the orientation of the selected anatomical feature of the body of the animal; (b) an orientation-determination module that comprises instructions for obtaining three-dimensional data for determining the orientation of the selected anatomical feature; (c) a position recorder in communication with the orientation-determination module, that comprises: (i) an attachment device; (ii) a measuring device comprising a gyroscope and an inclinometer that measures the orientation of a first position of the selected anatomical feature; wherein the inclinometer is configured to detect and measure yaw and the gyroscope is configured to detect and measure pitch and roll, and wherein the attachment device operably couples the measuring device to at least one part of the body of the animal that comprises the selected anatomical feature; and (iii) instructions for obtaining a plurality of three-dimensional positioning data from the measuring device to determine the orientation of the desired first position of the selected anatomical feature; (d) a first medical imaging device in communication with the orientation-determination module and with the position recorder, wherein the imaging device comprises instructions to obtain and generate a scan comprising a plurality of images of the at least one part of the body of the animal that comprises the selected anatomical feature in the desired first position; and (e) a device to display the plurality of generated images.

Preferably the system includes at least three fiducial markers operably coupled to the attachment device, such that the at least three fiducial markers create (a) a predetermined angle; and (b) a predetermined distance with respect to the measuring device, both of which are constant. In certain embodiments, the at least three fiducial markers preferably are made of a CT- or MRI-compatible material. Likewise, the attachment device preferably includes an attachment band adapted and configured to secure the device to the at least one part of the body of the animal. The system may also further include a database containing a plurality of positioning data that identify the first position of the at least one part of the body of the animal in three dimensions. Such a database may further include: (a) a computerized model of the position recorder; and (b) a plurality of positioning data that identifies a second position of the at least one part of the body of the animal distinct from that of the first position.

The database may further comprise a coupled image comprising the computerized model of the position recorder and the plurality of generated images. The database may also further include a re-oriented image wherein the scan comprising the plurality of images of the at least one part of the body of the animal is re-oriented in a desired anatomical position using the plurality of positioning data.

In a next embodiment, the invention also provides an apparatus for recording a first anatomical position of a selected body part of a patient, comprising: an attachment device, wherein the attachment device couples to at least one selected body part of the patient; and a measuring device, wherein the measuring device measures the orientation of a first anatomical position of the selected body part relative to a known landmark within the body of the patient; and a connector that couples the measuring device to the attachment device.

The orientation of the first anatomical position of the selected body part may be measured three-dimensionally using pitch, roll, and yaw data obtained from the measuring device, which may be a digital device, such as one that includes a gyroscope, an inclinometer, or a combination thereof.

In certain embodiments, the first anatomical position of the selected body part will include a natural position, and the apparatus will include at least three fiducial markers that are operably positioned relative to the connector at predetermined fixed distances and predetermined fixed angles relative to each other to define a three-dimensional space. As noted herein, these fiducial markers may comprise a CT- or an MRI-detectable material.

The attachment device may include an attachment band or a jig, such as an individualized occlusal bite registration, which may comprise a radiolucent material, such as a dental acrylic material.

In a further embodiment, the invention provides a method for recording a desired anatomical position of a first part of a patient's body in three-dimensions. Such a method includes at least the steps of: obtaining a position recorder comprising an attachment device and a measuring device (which preferably includes a gyroscope, an inclinometer, or a combination thereof) coupled to the attachment device; coupling the position recorder to the first part of the patient's body at one or more defined locations; orienting the patient's body to a desired anatomical position of a first part thereof; and recording the selected first part of the patient's body in three-dimensions, by typically monitoring the pitch, the yaw, and the role of the measuring device.

In a further embodiment, the invention provides a method of performing a medical procedure. In an overall and general sense, this method includes: obtaining a plurality of positioning data for the orientation of a first selected anatomical region of a patient using a position recorder, wherein the first selected anatomical region is oriented in a first, natural position; generating a computer model of the position recorder; scanning the first selected anatomical region of the patient using a CT scanner, wherein the first selected anatomical region is oriented in a second distinct non-natural position; creating a three-dimensional representation of the selected anatomical region of the patient; re-orienting the three-dimensional representation of the selected anatomical region to a natural body position; simulating a surgery to determine the post-surgery outcome; and performing the surgery.

BRIEF DESCRIPTION OF THE DRAWINGS

The following drawings form part of the present specification, and are included to further illustrate certain aspects of the invention. The invention may be better understood by reference to the following description taken in conjunction with the accompanying drawings, in which like reference numerals identify like elements, and in which:

FIG. 3 is a diagram of a database in accordance with an exemplary embodiment;

FIG. 10 is a flowchart of a method for determining a desired head orientation and position of a subject in accordance with an exemplary embodiment;

FIG. 11 illustrates a perspective view of an anatomic orientation and position recorder comprising an attachment device in accordance with an exemplary embodiment;

FIG. 12 illustrates a perspective view of an anatomic orientation and position recorder coupled to one or more teeth of a subject in accordance with an exemplary embodiment;

FIG. 13 is a flowchart of a method for recording a desired head orientation and position in three-dimensions and reorienting a head scan to the desired head orientation and position in accordance with an exemplary embodiment;

FIG. 18 is a flowchart of a method for performing surgery on a subject using a head CT scan that has been reoriented to a desired head orientation and position in accordance with an exemplary embodiment; and FIG. 19 is a flowchart of a method for radiation planning and treatment on a subject in accordance with an exemplary embodiment.

DESCRIPTION OF ILLUSTRATIVE EMBODIMENTS

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would, nevertheless, be a routine undertaking for those of ordinary skill in the art having the benefit of this disclosure.

There are several medical fields that require a desired anatomic orientation and position to be duplicated at a later time so as to facilitate and improve diagnosis and treatment. For example, the diagnosis and treatment of craniofacial deformities require correct head orientation and position, known as the "natural head position" ("NHP"). Other examples requiring a particular anatomic orientation and position include, without limitation, radiation therapy and dentistry.

NHP is the natural physiologic position of the head that is obtained when a relaxed subject looks at a distant reference. NHP is relevant to at least craniofacial morphology, future growth patterns, and modes of respiration. Various apparatuses and methods have been utilized for determining NHP, but each of the methods to date exhibit inherent problems, including instability, limited reproducibility, lack of accuracy, not accounting for asymmetries, limited information (dimensional limitations), measuring a static NHP, influencing head posture, alternating of the image and cost relative to reimbursement. Since there has been an increased utilization of three-dimensional diagnostic imaging, it has become more effective to provide a desired anatomic orientation and position in three-dimensions. Therefore, the development of a new method of recording a desired anatomic orientation and position is warranted.

Figure 1:
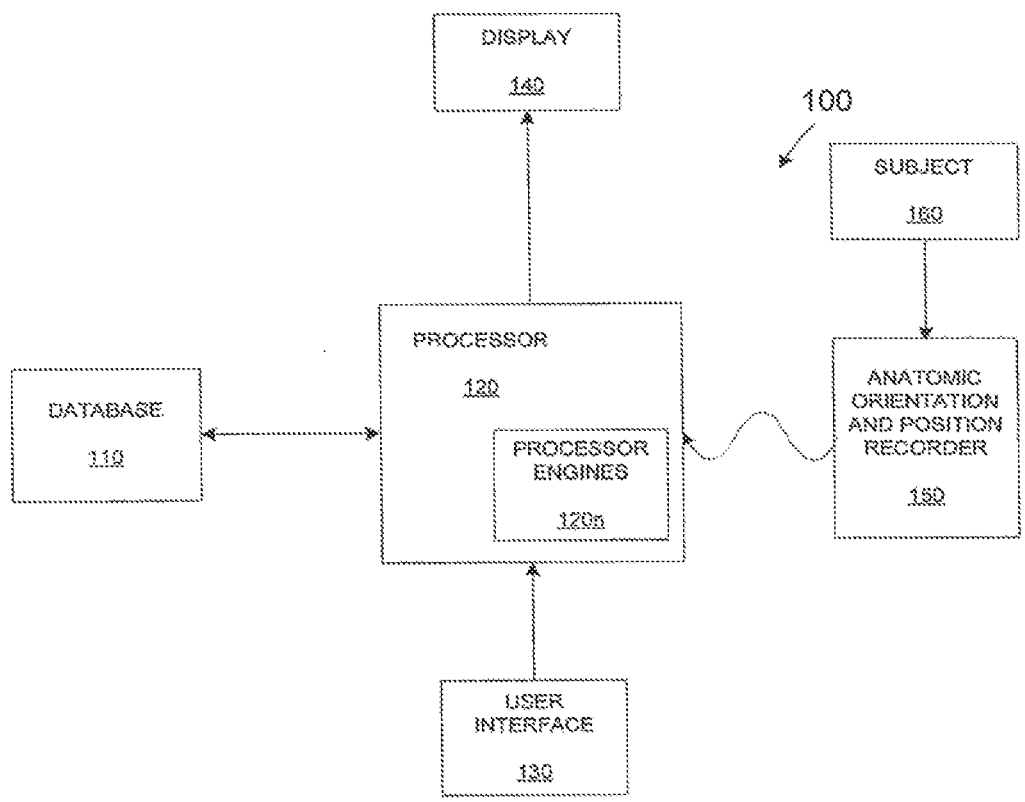
FIG. 1 is a block diagram of an anatomic orientation and position detector system in accordance with an exemplary embodiment.

FIG. 1 illustrates a block diagram of an anatomic orientation and position detector system in accordance with an exemplary embodiment. This exemplary embodiment disclosed hereinbelow describes an anatomic orientation and position detector system 100 specifically designed to obtain a desired anatomic orientation and position and reorient an anatomic scan to the desired anatomic orientation and position. This reorientation of the anatomic scan may assist the medical provider in diagnosing and treating a subject 160. The subject 160 may be a human or an animal. This anatomic orientation and position detector system 100 also allows a medical provider to duplicate the desired anatomic orientation and position from one point in time to another point in time. The anatomic orientation and position detector system 100 comprises a database 110, a processor 120 comprising one or more processor engines 120$n$, a user interface 130, a display 140, and an anatomic orientation and position recorder 150. Although the detailed description below describes the anatomic orientation and position recorder 150 being used to gather data for the orientation and position of a subject's 160 head, the anatomic orientation and position recorder 150 may be used to gather the orientation and position data for any anatomic part of a subject 160.

Figure 2:
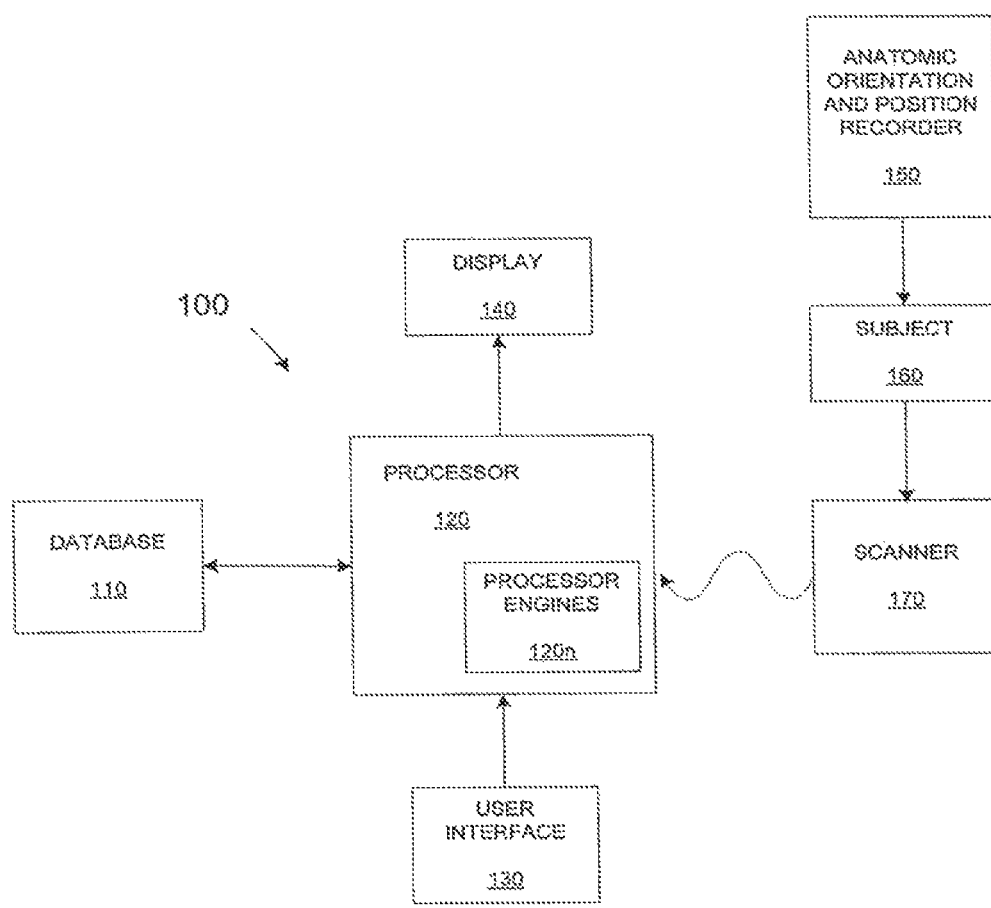
FIG. 2 is a block diagram of an anatomic orientation and position detector system comprising a scanner in accordance with an exemplary embodiment.

FIG. 2 illustrates a block diagram of an anatomic orientation and position detector system comprising a scanner in accordance with an exemplary embodiment. As illustrated here, the anatomic orientation and position detector system 100 may further comprise a scanner 170 in communication with the processor 120 in accordance with an exemplary embodiment.

Referring to FIG. 1 and FIG. 2, the anatomic orientation and position recorder 150, the display 140, the user interface 130 and the scanner 170 is described hereinbelow. The anatomic orientation and position recorder 150 may be coupled to the subject 160 to gather and record the one or more head orientation and position data. As stated above, the anatomic orientation and position recorder 150 may be used to gather and record the orientation and position data for any anatomic part, not only the subject's 160 head. This anatomic orientation and position recorder 150 may be in communication with the processor 120. In this embodiment, the anatomic orientation and position recorder 150 is in wireless communication with the processor 120. Although this embodiment shows the anatomic orientation and position recorder 150 to be in wireless communication with the processor 120, this communication may be via wire without departing from the scope and spirit of the exemplary embodiment. Additionally, the anatomic orientation and position recorder 150 may have a storage space wherein the one or more head orientation and position data may be stored on the storage space such that it may later be transferred to the database 110.

The display 140 may be used for showing at least the anatomic orientation and position recorder image and a head scan comprising the anatomic orientation and position recorder 150. Although this embodiment uses a head scan, a scan of any anatomic part may be used without departing from the scope and spirit of the exemplary embodiment. The display 140 may allow the user to visually determine the proper coupling of the anatomic orientation and position recorder image to the head scan comprising the anatomic orientation and position recorder 150. The display 140 may be a monitor, projector screen, television unit, an LCD screen, or any other type of screen or surface that allows an image to be displayed.

The user interface 130 allows the user to interface with the anatomic orientation and position detector system 100. The user interface 130 may comprise a keyboard, mouse, touch screen or any other user interface device for communicating with the anatomic orientation and position detector system 100.

In one embodiment, this scanner 170 comprises a CT scanner. The CT scanner may scan the subject's 160 head and the anatomic orientation and position recorder 150, wherein the anatomic orientation and position recorder 150 is coupled to the subject 160. The resulting scan may be displayed on the display 140 and/or stored within the database 110. Although this embodiment uses a CT scanner, any imaging modality may be used without departing from the scope and spirit of the exemplary embodiment.

Figure 3:
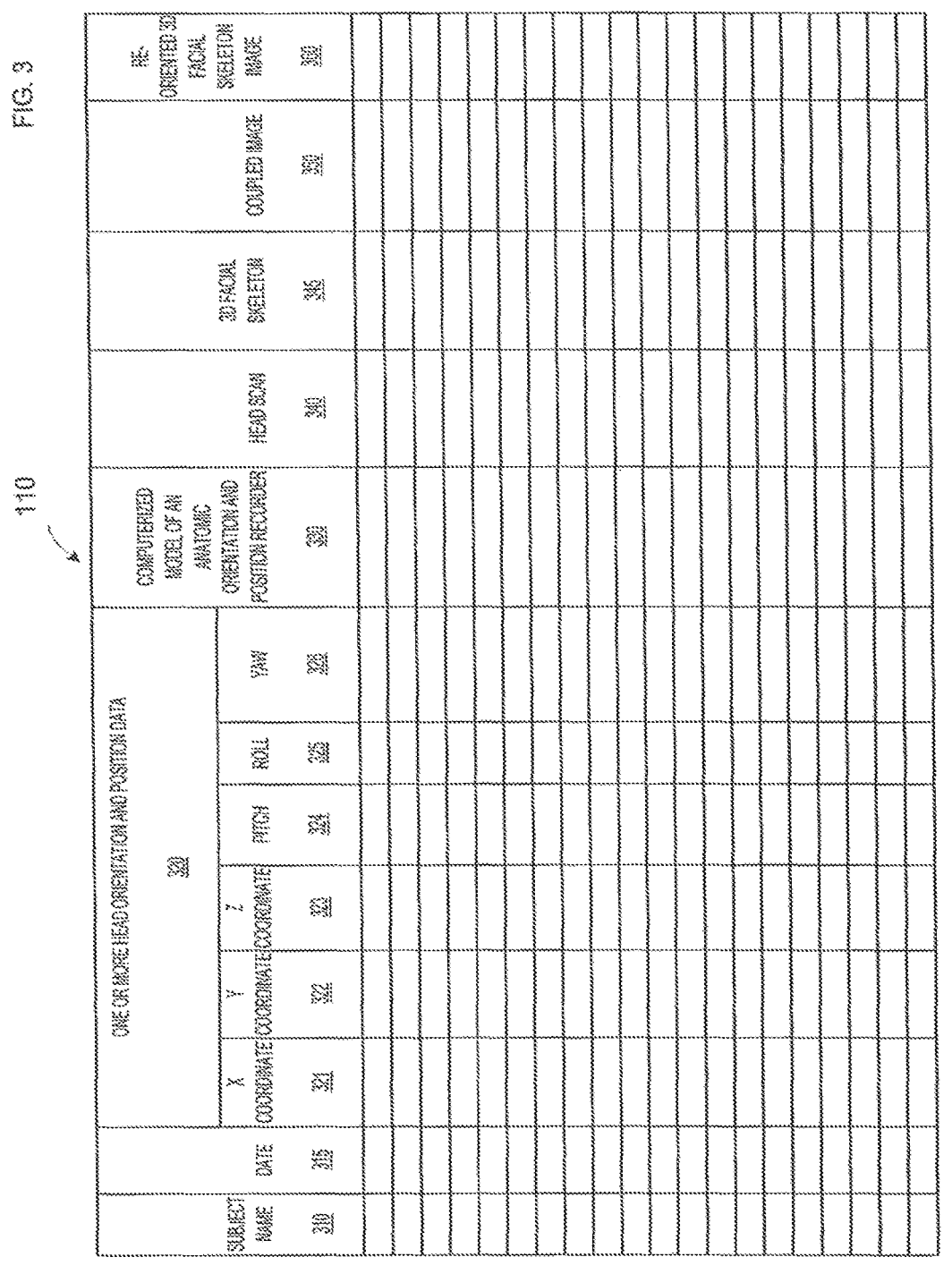

FIG. 3 illustrates a diagram of a database in accordance with an exemplary embodiment. Referring to FIG. 1, FIG. 2 and FIG. 3, the database 110 comprises a subject name 310, a date 315, one or more head orientation and position data 320 comprising an X coordinate 321, a Y coordinate 322, a Z coordinate 323, a pitch 324, a roll 325, and a yaw 326, a computerized model of an anatomic orientation and position recorder 330, a head scan 340, a 3D facial skeleton 345, a coupled image 350, and a re-oriented 3D facial skeleton image 360. The database 110 is organized such that the one or more head orientation and position data 320, the computerized model of the anatomic orientation and position recorder 330, the head scan 340, the 3D facial skeleton 345, the coupled image 350, and the re-oriented 3D facial skeleton image 360 are associated with the subject name 310. Again, although this embodiment uses a head scan, a 3D facial skeleton and a re-oriented 3D facial skeleton image, any anatomic part may be used without departing from the scope and spirit of the exemplary embodiment.

The one or more head orientation and position data 320 comprises the X coordinate 321, the Y coordinate 322, the Z coordinate 323, the pitch 324, the roll 325 and the yaw 326 recorded from the anatomic orientation and position recorder 150 while the subject's head is in a desired head orientation and position. The computerized model of the anatomic orientation and position recorder 330 may be a substantially exact computer-generated representation of the anatomic orientation and position recorder 150. The computerized model of the anatomic orientation and position recorder 330 may be scanned into the database 110 or may be manually re-created within the anatomic orientation and position detector system 100 and stored within the database 110. The head scan 340 of the subject 160 may be a head CT scan wherein the anatomic orientation and position recorder 150 is visually shown in the head scan 340. Although the head scan 340 of the subject 160 may be a head CT scan, other types of scans may be used without departing from the scope and spirit of the exemplary embodiment. The 3D facial skeleton 345 may be generated from the head scan 340. The coupled image 350 may be generated via the coupling of the computerized model of an anatomic orientation and position recorder 330 and the 3D facial skeleton 345. The re-oriented 3D facial skeleton image 360 may be generated from the coupled image 350 using surface geometry and/or at least one fiducial marker that may be coupled to the anatomic orientation and position recorder 150, and/or the one or more head orientation and position data 320.

Figure 4:
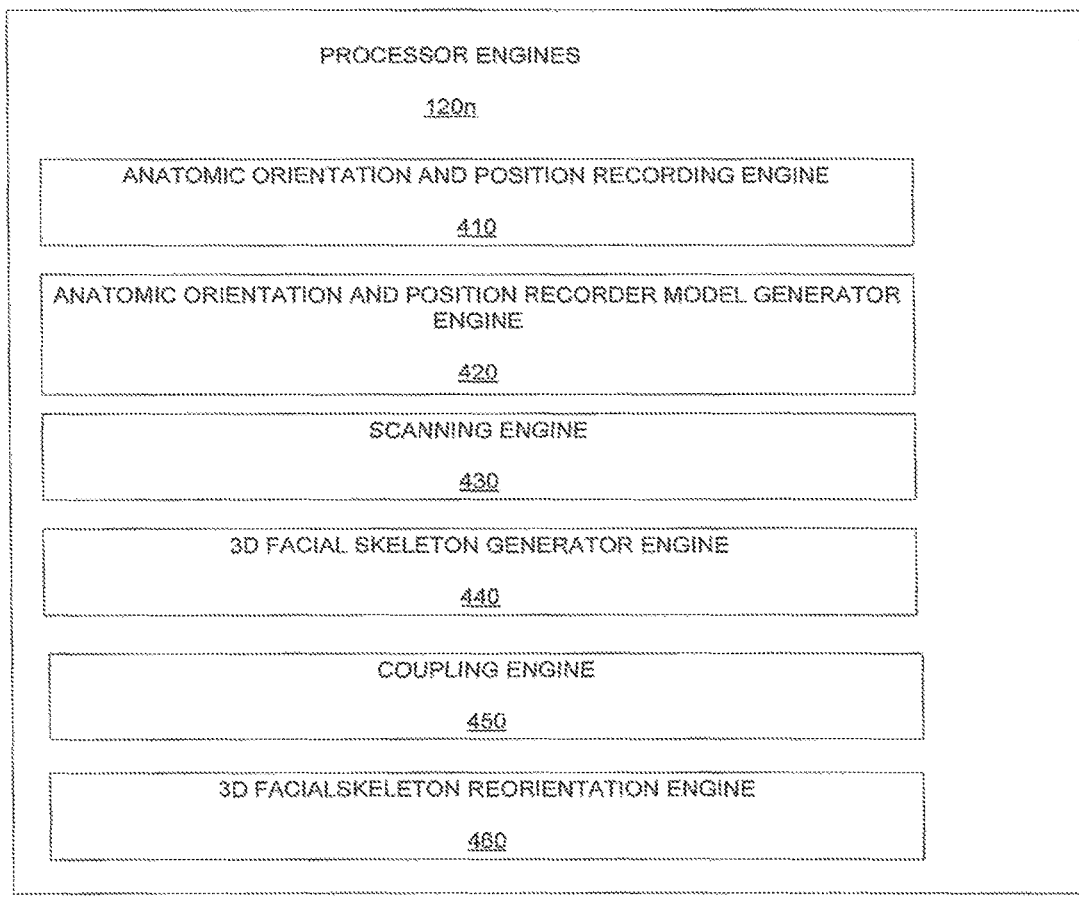
FIG. 4 is a block diagram of one or more processor engines within the computer system in accordance with an exemplary embodiment.

FIG. 4 illustrates a block diagram of one or more processor engines 120$n$ located within the processor 120 in accordance with an exemplary embodiment. As shown in this embodiment, the one or more processor engines 120$n$ comprise an anatomic orientation and position recording engine 410, an anatomic orientation and position recorder model generator engine 420, a scanning engine 430, a 3D facial skeleton generator engine 440, a coupling engine 450 and a 3D facial skeleton reorientation engine 460. Additional engines may be used depending upon the anatomic part being scanned and the images being manipulated.

Referring to FIG. 1, FIG. 2, FIG. 3 and FIG. 4, the anatomic orientation and position recording engine 410 collects one or more head orientation and position data 320 from the anatomic orientation and position recorder 150 while the anatomic orientation and position recorder 150 is coupled to the subject 160 and the subject's head is in the desired head orientation and position. Once the one or more head orientation and position data 320 is collected, the anatomic orientation and position recording engine 410 records the desired head orientation and position into the database 110. The one or more head orientation and position data 320 comprises the X coordinate 321, the Y coordinate 322, the Z coordinate 323, the pitch 324, the roll 325 and the yaw 326 of the anatomic orientation and position recorder 150, while the subject's head is in the desired head orientation and position.

The anatomic orientation and position recorder model generator engine 420 generates a computerized model of the anatomic orientation and position recorder 330. The anatomic orientation and position recorder model generator engine 420 scans the anatomic orientation and position recorder 150, generates a computerized model of the anatomic orientation and position recorder 330 and stores the computerized model of the anatomic orientation and position recorder 330 within the database 110. The scanner used in this embodiment may be any scanner capable of scanning and producing a computerized model of the anatomic orientation and position recorder 330 without departing from the scope and spirit of the exemplary embodiment. In this embodiment, the computerized model of the anatomic orientation and position recorder 330 may be scanned three-dimensionally.

The scanning engine 430 scans the subject's head and the anatomic orientation and position recorder 150, wherein the anatomic orientation and position recorder 150 is coupled to the subject 160 and the subject's head is oriented in a second head orientation and position. In this embodiment, the scanner 170 used is a CT scanner. Although a CT scanner is used for scanning the subject's head and the anatomic orientation and position recorder 150 while the subject's head is oriented in the second head orientation and position, any scanner capable of performing the scan may be used without departing from the scope and spirit of the exemplary embodiment. In this embodiment, the scan may be performed such that the data provides three-dimensional information. In addition, once the head scan 340 is collected, the head scan 340 is stored within the database 110. Although this embodiment uses the scanning engine 430 to scan the subject's head, any anatomic feature may be scanned without departing from the scope and spirit of this embodiment.

The 3D facial skeleton generator engine 440 generates a 3D facial skeleton 345 from the head scan 340, which has been stored in the database 110. The 3D facial skeleton generator engine 440 generates a 3D facial skeleton 345 that comprises the subject's head and the anatomic orientation and position recorder 150, which is coupled to the subject 160. The 3D facial skeleton 345 is stored within the database 110. Although this embodiment uses the 3D facial skeleton generator engine 440 to generate the 3D facial skeleton 345, the underlying skeletal structure of any anatomic feature may be generated depending upon the anatomic feature scanned by the scanning engine 430 without departing from the scope and spirit of this embodiment.

The coupling engine 450 couples the computerized model of the anatomic orientation and position recorder 330 to the 3D facial skeleton 345. The coupling engine 350 provides a single image or an overlapping image wherein the computerized model of the anatomic orientation and position recorder 330 and the 3D facial skeleton 345 can both be manipulated independently of each other, but within the same image or overlapping image.

The 3D facial skeleton reorientation engine 460 reorients the 3D facial skeleton 345 using the one or more head orientation and position data 320 obtained from the anatomic orientation and position recording engine 410. The 3D facial skeleton 345 is an image created while the subject's head is in the second head orientation and position. The one or more head orientation and position data 320, which includes the X coordinate 321, the Y coordinate 322, the Z coordinate 323, the pitch 324, the roll 325 and the yaw 326, provides three-dimensional orientation and position information that was taken while the subject's head was oriented in the desired head orientation and position. The user employs this head orientation and position data 320 and the coupled image 350 to reorient the 3D facial skeleton 345 from the second head orientation and position to the desired head orientation and position.

It should be understood that there may be engines that perform multiple tasks or that there may be multiple engines that perform a single task without departing from the scope and spirit of the exemplary embodiment. Additionally, it should be understood that there may be additional engines used for reorienting a subject's head from the second head orientation and position to the desired head orientation and position without departing from the scope and spirit of the exemplary embodiment.

Figure 5:
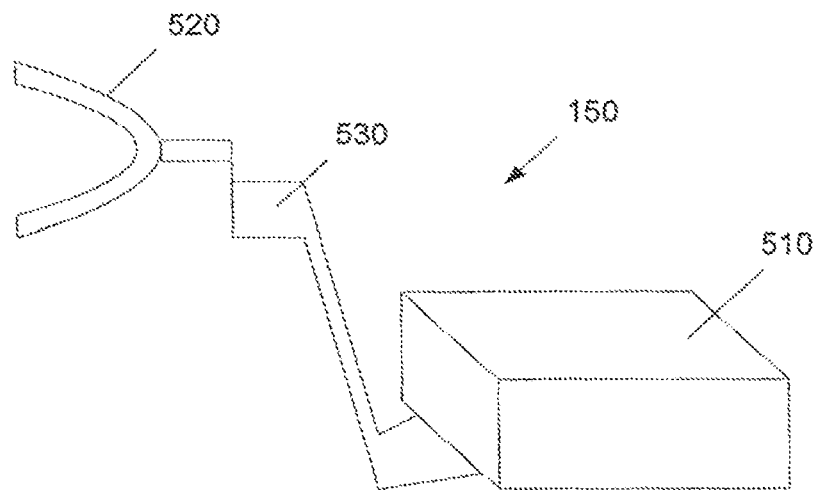
FIG. 5 illustrates a perspective view of an anatomic orientation and position recorder comprising an attachment device in accordance with an exemplary embodiment.

FIG. 5 illustrates a perspective view of an anatomic orientation and position recorder 150 comprising an attachment device 520 in accordance with an exemplary embodiment. In this embodiment, the anatomic orientation and position recorder 150 comprises a measuring device 510 and an attachment device 520. In this embodiment, the anatomic orientation and position recorder 150 may also comprise a connector 530 for coupling the measuring device 510 to the attachment device 520. The measuring device 510 measures the one or more head orientation and position data comprising the X coordinate, the Y coordinate, the Z coordinate, the pitch, the roll and the yaw. In addition, the distances and the angles from the measuring device 510 to the subject's head remain constant so long that the anatomic orientation and position recorder 150 remains securely coupled to the subject and the subject's head remains relatively still. The measuring device 510 may comprise a storage device for storing the one or more head orientation and position data so that they may be transferred to the database at a later time. In this embodiment, the measuring device 510 comprises a gyroscope. The gyroscope rotates in various angles and measures the X coordinate, the Y coordinate, the Z coordinate, the pitch, the roll and the yaw of the gyroscope. Although this embodiment uses a gyroscope as the measuring, device, other measuring devices, including but not limited to an inclinometer, may be used without departing from the scope and spirit of the exemplary embodiment. Additionally, the measuring device 510 may be either analog or digital.

The attachment device 520 couples the anatomic orientation and position recorder 150 to the subject. The attachment device 520 may provide a stable attachment to the subject so that any movement or vibrations are minimized during the anatomic orientation and position recorder's 150 operation. In this embodiment, the attachment device 520 comprises a bite-jig. The bite-jig is individualized to the one or more teeth of the subject so that the coupling of the bite-jig to the subject's one or more teeth is secure and stable.

Figure 6:
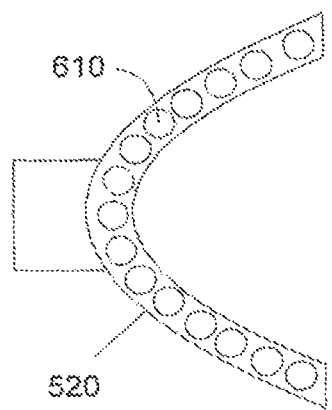
FIG. 6 illustrates a top view of a bite-jig in accordance with an exemplary embodiment.

FIG. 6 illustrates a top view of the bite-jig in accordance with an exemplary embodiment. Referring to FIG. 5 and FIG. 6, it may be seen that the bite-jig comprises an individualized occlusal bite registration 610, which may be present at the top and/or the bottom of the bite-jig. Although this embodiment uses a bite-jig as the attachment device 520, the attachment device 520 may comprise any device capable of providing a secure and stable attachment to any anatomic part, including but not limited to a screw into the subject's bone, a permanent or temporary attachment to the subject, or a permanent or temporary attachment to an equipment, such as a table, chair or platform, without departing from the scope and spirit of the exemplary embodiment. In addition, the attachment device comprises a radiolucent material, which may be capable of being scanned. The radiolucent material used in this embodiment comprises a dental acrylic material. Although a dental acrylic material may be used, other radiolucent materials may be used without departing from the scope and spirit of the exemplary embodiment. Alternatively, the attachment device may comprise radiopaque material depending upon its application.

The connector 530 couples the attachment device 520 to the measuring device 510. The connector 530 may be formed of a suitable material capable of minimizing the movement and vibrations of the anatomic orientation and position recorder 150. In this embodiment, the connector 530 is not formed of a radiolucent material, thereby not being scannable. Although this embodiment uses a connector that is not formed with a radiolucent material, a radiolucent material may be used, so long as the movement and vibrations of the anatomic orientation and position recorder 150 are minimized, without departing from the scope and spirit of the exemplary embodiment. Alternatively, the connector may comprise radiopaque material depending upon its application.

Figure 7:
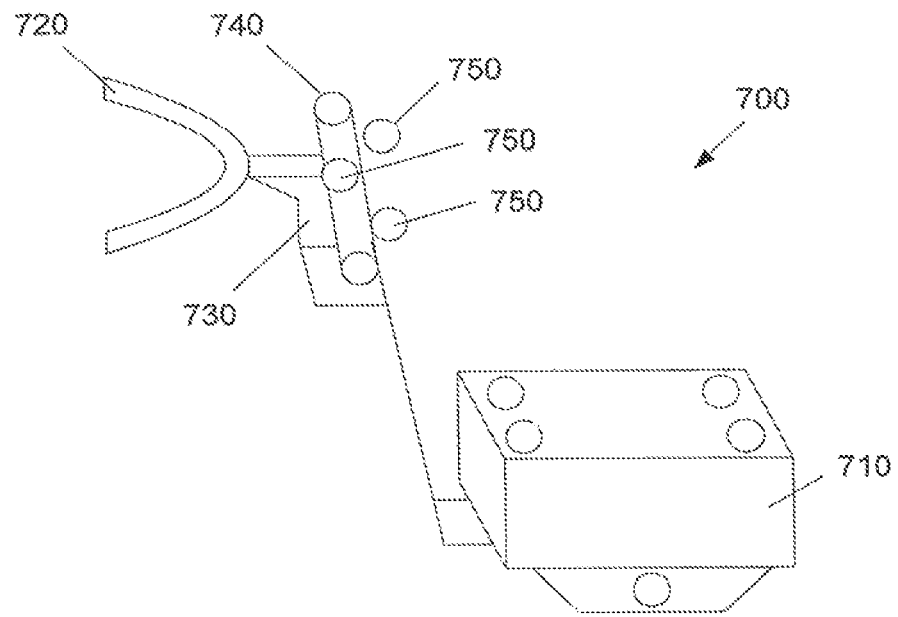
FIG. 7 illustrates a perspective view of an anatomic orientation and position recorder comprising at least one fiducial marker in accordance with an exemplary embodiment.

FIG. 7 illustrates a perspective view of an anatomic orientation and position recorder 700 comprising at least one fiducial marker 750 in accordance with an exemplary embodiment. In this embodiment, the anatomic orientation and position recorder 700 comprises a measuring device 710, an attachment device 720, a connector 730, a fiducial holder 740 and at least one fiducial marker 750. The measuring device 710 measures the one or more head orientation and position data comprising the X coordinate, the Y coordinate, the Z coordinate, the pitch, the roll and the yaw. In addition, the distances and the angles from the measuring device 710 to, the subject's head remain constant so long that the anatomic orientation and position recorder 700 remains securely coupled to the subject and the subject's head remains relatively still. The measuring device 710 may comprise a storage device for storing the one or more head orientation and position data so that they may be transferred to the database at a later time. In this embodiment, the measuring device 710 comprises a gyroscope. The gyroscope rotates in various angles and measures the X coordinate, the Y coordinate, the Z coordinate, the pitch, the roll and the yaw of the gyroscope. Although this embodiment uses a gyroscope as the measuring device 710, other measuring devices, including but not limited to an inclinometer, may be used without departing from the scope and spirit of the exemplary embodiment.

The attachment device 720 couples the anatomic orientation and position recorder 700 to the subject. The attachment device 720 may provide a stable attachment to the subject so that any movement or vibrations are minimized during the anatomic orientation and position recorder's 700 operation. In this embodiment, the attachment device 720 comprises a bite-jig. The bite-jig is individualized to the subject's teeth so that the coupling of the bite-jig to the subject's teeth is secure and stable. As illustrated and described in FIG. 6, the bite-jig comprises an individualized occlusal bite registration 610, which may be present at the top and/or the bottom of the bite-jig. Although this embodiment uses a bite-jig as the attachment device 520, the attachment device 520 may comprise any device capable of providing a secure and stable attachment to any anatomic part, including but not limited to a screw into the subject's bone, a permanent or temporary attachment to the subject, or a permanent or temporary attachment to an equipment, such as a table, chair or platform, without departing from the scope and spirit of the exemplary embodiment. Also, the attachment device 720 comprises a radiolucent material which may be capable of being scanned. The radiolucent material used in this embodiment comprises a dental acrylic material. Although a dental acrylic material may be used, other radiolucent materials may be used without departing from the scope and spirit of the exemplary embodiment. Alternatively, the attachment device may comprise radiopaque material depending upon its application.

The connector 730 couples the attachment device 720 to the measuring device 710. The connector 730 may be formed of a suitable material capable of minimizing the movement and vibrations of the anatomic orientation and position recorder 700. In this embodiment, the connector 730 is not formed of a radiolucent material, thereby not being scannable. Although this embodiment uses a connector 730 that is not formed of a radiolucent material, a radiolucent material may be used, so long as the movement and vibrations of the anatomic orientation and position recorder 700 are minimized, without departing from the scope and spirit of the exemplary embodiment. Alternatively, the connector may comprise radiopaque material depending upon its application.

The fiducial holder 740 is coupled to the connector 730 and may be formed of a suitable material capable of minimizing the movement and vibrations of the anatomic orientation and position recorder 700. In this embodiment, the fiducial holder 740 is positioned in a manner such that when the attachment device 720 is coupled to the subject's teeth, the fiducial holder 740 runs widthwise across the subject's head. Although this embodiment illustrates the fiducial holder 740 running widthwise of the subject's head, the fiducial holder 740 may run in any direction, including lengthwise, depth wise, widthwise or any combination of lengthwise, widthwise, or depth wise, without departing from the scope and spirit of the exemplary embodiment. In this embodiment, the fiducial holder 740 is not formed of a radiolucent material, thereby not being scannable. Although this embodiment uses a fiducial holder 740 that is not formed of a radiolucent material, a radiolucent material may be used, so long as the movement and vibrations of the anatomic orientation and position recorder 700 are minimized, without departing from the scope and spirit of the exemplary embodiment. Alternatively, the fiducial holder may comprise radiopaque material depending upon its application.

The at least one fiducial marker 750 is coupled to the fiducial holder 740. When two or more fiducial markers 750 are coupled to the fiducial holder 740, the fiducial markers 750 are positioned and oriented at various angles and distances from the fiducial holder 740. These fiducial markers 750 assist the user in reorienting the 3D facial skeleton that is in the second head orientation and position to the desired head orientation and position using the one or more head orientation and position data and/or surface geometry. In this embodiment, although three fiducial markers 750 are coupled to the fiducial holder 740, more or less fiducial markers 750 may, be coupled to the fiducial holder 740 without departing from the scope and spirit of the exemplary embodiment. Additionally, the at least one fiducial marker 750 comprises a radiolucent material which may be capable of being scanned. The radiolucent material used in this embodiment comprises a dental acrylic material. Although a dental acrylic material may be used, other radiolucent materials may be used without departing from the scope and spirit of the exemplary embodiment. Alternatively, the fiducial markers may comprise radiopaque material depending upon its application. In an x-ray scanner or a CT scanner, the material of the fiducial markers may be radiopaque. In a laser scanner, the material of the fiducial markers may be opaque.

Figure 8:
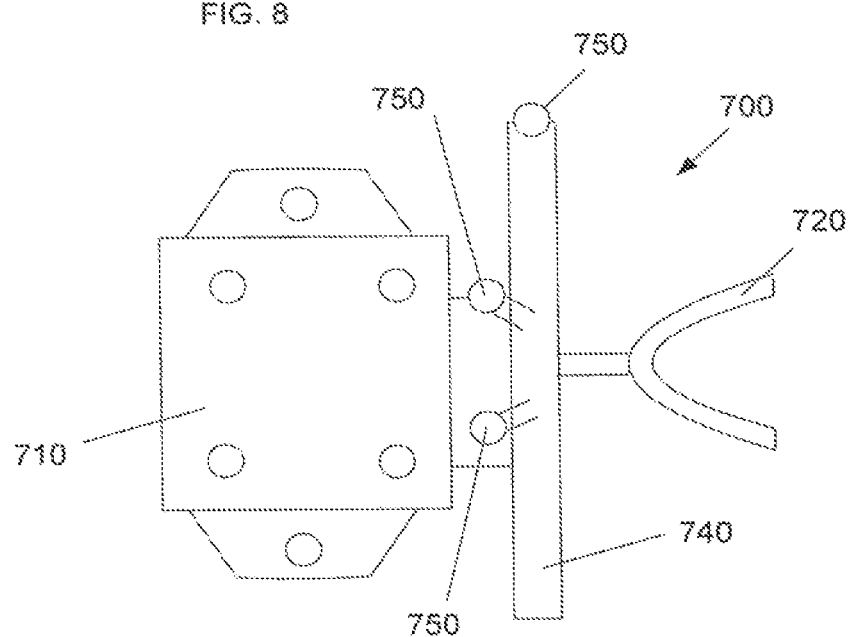
FIG. 8 illustrates a top view of an anatomic orientation and position recorder comprising at least one fiducial marker in accordance with an exemplary embodiment.

FIG. 8 illustrates a top view of an anatomic orientation and position recorder 700 comprising at least one fiducial marker 750 in accordance with an exemplary embodiment.

Figure 9:
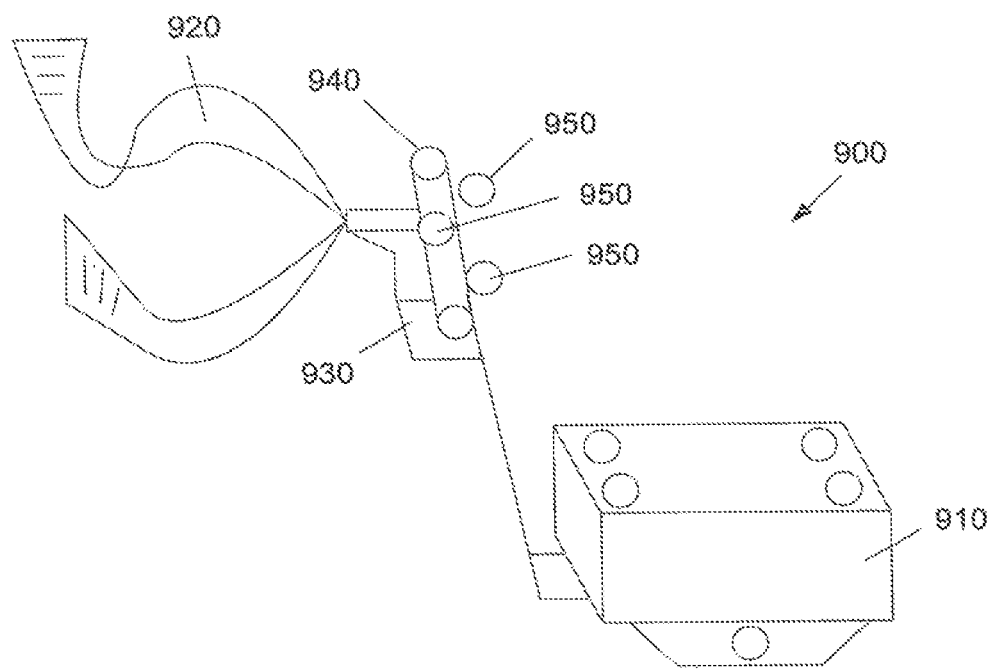
FIG. 9 illustrates a perspective view of an anatomic orientation and position recorder comprising an attachment band in accordance with an exemplary embodiment.

FIG. 9 illustrates a perspective view of an anatomic orientation and position recorder 900 comprising an attachment band 920 in accordance with an exemplary embodiment. The anatomic orientation and position recorder 900 illustrated in FIG. 9 is similar to the anatomic orientation and position recorder as illustrated in FIG. 7, except that the attachment device comprises an attachment band 920, in lieu of the bite-jig 720 (FIG. 7). The attachment band 920 couples the anatomic orientation and position recorder 900 to the subject. The attachment band 920 may provide a stable attachment to the subject so that any movement or vibrations are minimized during the anatomic orientation and position recorder's 900 operation. In this embodiment, the attachment band 920 is shown to attach using a hook and loop attachment, such as Velcro®. Although this embodiment shows the attachment band 920 to use a hook-and-loop attachment, the attachment band 920 may use any other attaching means, including but not limited to a button, a snap-on connector, or an adjustable attachment, without departing from the scope and spirit of the exemplary embodiment. The attachment band 920 comprises a radiolucent material that may be bendable and capable of being scanned. Although a radiolucent material is used, any material may be used without departing from the scope and spirit of the exemplary embodiment.

Referring now to FIG. 10, FIG. 11 and FIG. 12, a method 1000 for recording a desired head orientation and position of a subject in three-dimensions will now be described. FIG. 10 illustrates a flowchart of a method for determining a desired head orientation and position of a subject in accordance with an exemplary embodiment. At step 1010, an anatomic orientation and position recorder comprising an attachment device and a measuring device coupled to the attachment device is obtained. Exemplary anatomic orientation and position recorders have been described above. FIG. 11 illustrates a perspective view of an anatomic orientation and position recorder 150 comprising an attachment device 520 in accordance with an exemplary embodiment. The measuring device 510 may comprise a gyroscope for obtaining three-dimensional head orientation and position data comprising the X-coordinate, the Y-coordinate, the Z-coordinate, i.e., the pitch, the roll and the yaw. Other measuring devices may be used, including, but not limited to, an inclinometer, without departing from the scope and spirit of the exemplary embodiment. Additionally, the measuring device may be either digital or analog without departing from the scope and spirit of the exemplary embodiment.

At step 1020, the anatomic orientation and position recorder is coupled to a body part of a subject at a particular location. The anatomic orientation and position recorder may be coupled to the subject's body via any coupling device, including but not limited to an attachment band or a bite-jig, without departing from the scope or spirit of the exemplary embodiment. FIG. 12 illustrates a perspective view of an anatomic orientation and position recorder 1200 coupled to one or more teeth 1240 of a subject in accordance with an exemplary embodiment. FIG. 12 shows the anatomic orientation and position recorder 1200 comprising a bite-jig 1220, a gyroscope 1210, and a connector 1230 coupling the gyroscope 1210 to the bite-jig 1220.

At step 1030, the subject's head is oriented to a desired head orientation and position. This desired head orientation and position may be the natural head orientation and position or any other desired head orientation and position.

At step 1040, the desired head orientation and position is recorded three-dimensionally. The gyroscope measures one or more head orientation and position data comprising the X coordinate, the Y coordinate, the Z coordinate, the pitch, the roll and the yaw of the measuring device as it rotates about. The distances and the angles from the measuring device to the attachment device are constant and predetermined.

Figure 14:
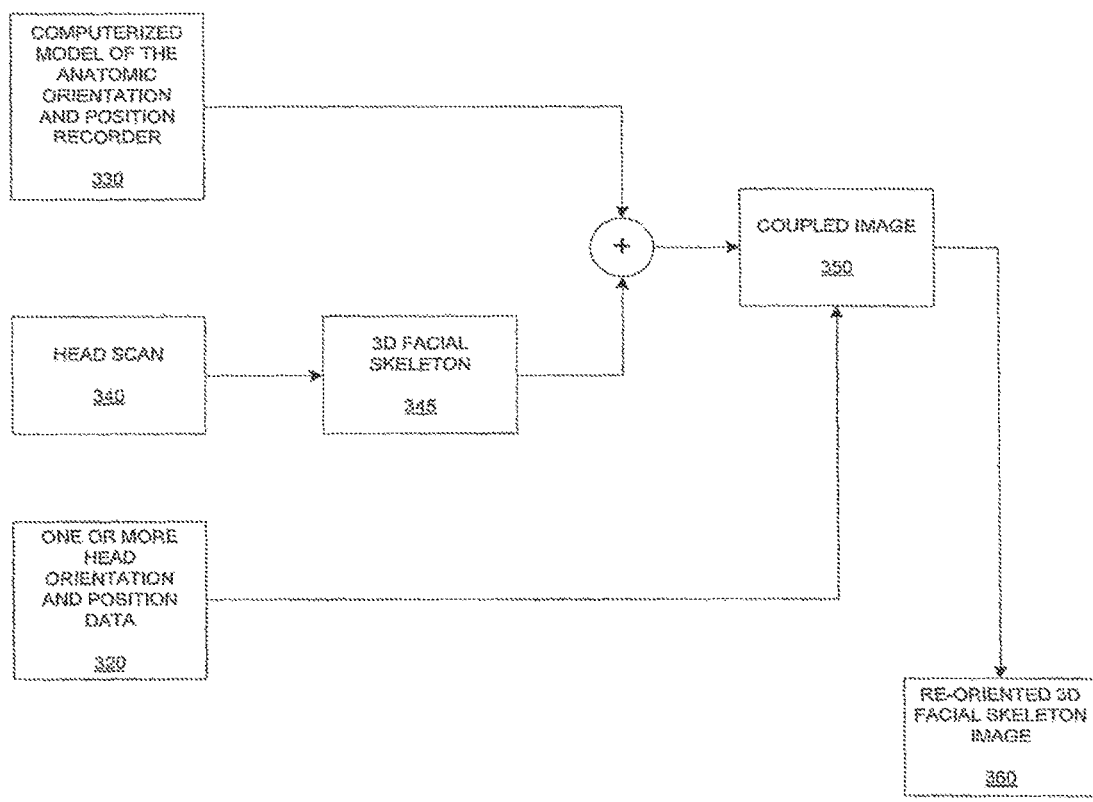
FIG. 14 is a block diagram showing steps 1340, 1350, 1360, 1370, 1380 and 1390 of FIG. 13 in accordance with an exemplary embodiment.

Referring now to FIG. 12, FIG. 13 and FIG. 14, a method 1300 for recording a desired head orientation and position in three-dimensions and reorienting a head scan to the desired head orientation and position will now be described. FIG. 14 illustrates a block diagram showing steps 1340, 1350, 1360, 1370, 1380 and 1390 of FIG. 13 in accordance with an exemplary embodiment. At step 1310, an anatomic orientation and position recorder is obtained, wherein the anatomic orientation and position recorder comprises an attachment device, wherein the attachment device is attachable to a body part of a subject, and a measuring device coupled to the attachment device, wherein the measuring device records a desired head orientation and position. Exemplary anatomic orientation and position recorders have been previously described above.

At step 1320, the anatomic orientation and position recorder is coupled to the body part at a particular location. The anatomic orientation and position recorder may be coupled to the subject's body via any coupling device, including but not limited to an attachment band or a bite-jig, without departing from the scope or spirit of the exemplary embodiment. FIG. 12, which has been previously described, illustrates a perspective view of an anatomic orientation and position recorder 1200 coupled to one or more teeth 1240 of a subject in accordance with an exemplary embodiment. FIG. 12 shows the anatomic orientation and position recorder 1200 comprising a bite-jig 1220, a gyroscope 1210, and a connector 1230 coupling the gyroscope 1210 to the bite-jig 1220.

At step 1330, the subject's head is oriented to the desired head orientation and position. This desired head orientation and position may be the natural head orientation and position or any other desired head orientation and position.

At step 1340, the desired head orientation and position is recorded in a computer. The gyroscope measures one or more head orientation and position data 320 comprising the X coordinate, the Y coordinate, the Z coordinate, the pitch, the roll and the yaw of the measuring device as it rotates about. The distances and the angles from the measuring device to the attachment device are constant and predetermined. The one or more head orientation and position data 320 may be recorded and stored within the database.

At step 1350, a computerized model of the anatomic orientation and position recorder is generated. The computerized model of the anatomic orientation and position recorder 330 may be a substantially exact computer-generated representation of the anatomic orientation and position recorder. The computerized model of the anatomic orientation and position recorder 330 may be scanned into the database or may be manually recreated within the anatomic orientation and position detector system and stored within the database.

At step 1360, the head is scanned, wherein the anatomic orientation and position recorder is coupled to the body part at the particular location and wherein the head is oriented in a second orientation and position. The scanner may comprise a CT scanner. The CT scanner may scan the subject's head and the anatomic orientation and position recorder, wherein the anatomic orientation and position recorder 1200 is coupled to the subject 160. The resulting head scan 340 may be displayed on the display and/or stored within the database. Although this embodiment scans the subject's head, any anatomic feature may be scanned without departing from the scope and spirit of this embodiment.

At step 1370, a three-dimensional representation of the 3D facial skeleton 345 of the subject comprising the anatomic orientation and position recorder is created. This three-dimensional representation of the 3D facial skeleton 345 is generated from the head scan 340 of step 1360. The 3D facial skeleton 345 may be stored within the database. Although this embodiment generates the 3D facial skeleton 345, the underlying skeletal structure of any anatomic feature may be generated depending upon the anatomic feature scanned at step 1360 without departing from the scope and spirit of this embodiment.

At step 1380, the computerized model of the anatomic orientation and position recorder 330 is coupled to the three-dimensional representation of the 3D facial skeleton 345. A coupled image 350 results therefrom, wherein the user may manipulate either of the two images independently of one another. This coupled image 350 may be stored within the database.

At step 1390, the three-dimensional representation of the 3D facial skeleton is reoriented to the desired head orientation and position. The one or more head orientation and position data 320 is used in conjunction with the coupled image 350 to generate the re-oriented 3D facial skeleton image 360. The 3D facial skeleton 345 within the coupled image 350 is reoriented to the desired orientation and position resulting in the re-oriented 3D facial skeleton image 360. In addition, surface geometry may be used in this re-orientation process in lieu of the one or more head orientation and position data 320, or in combination with it.

Figure 15:
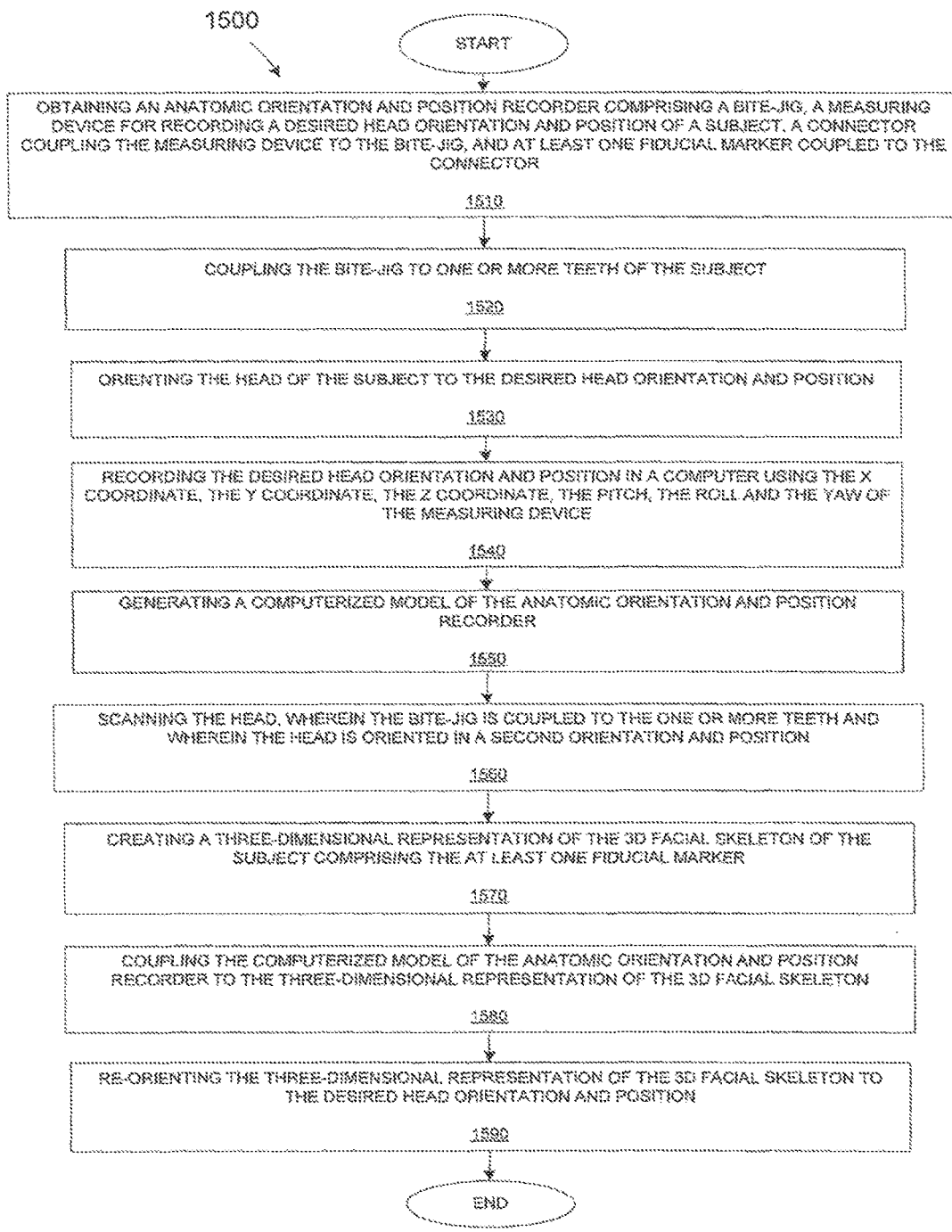
FIG. 15 is a flowchart of a method for recording a desired head orientation and position in three-dimensions and reorienting a head scan to the desired head orientation and position in accordance with an exemplary embodiment.

Referring now to FIG. 14, FIG. 15, FIG. 16 and FIG. 17, a method 1500 for recording a desired head orientation and position in three-dimensions and reorienting a head scan to the desired head orientation and position will now be described. FIG. 15 illustrates a flowchart of a method for recording a desired head orientation and position in three-dimensions and reorienting a head scan to the desired head orientation and position in accordance with an exemplary embodiment. FIG. 14 illustrates a block diagram showing steps 1340, 1350, 1360, 1370, 1380 and 1390 of FIG. 13 in accordance with an exemplary embodiment. At step 1510, an anatomic orientation and position recorder is obtained, wherein the anatomic orientation and position recorder comprises a bite-jig, a measuring device for recording a desired head orientation and position of a subject, a connector coupling the measuring device to the bite-jig, and at least one fiducial marker coupled to the connector. Exemplary anatomic orientation and position recorders have been previously described above.

Figure 16:
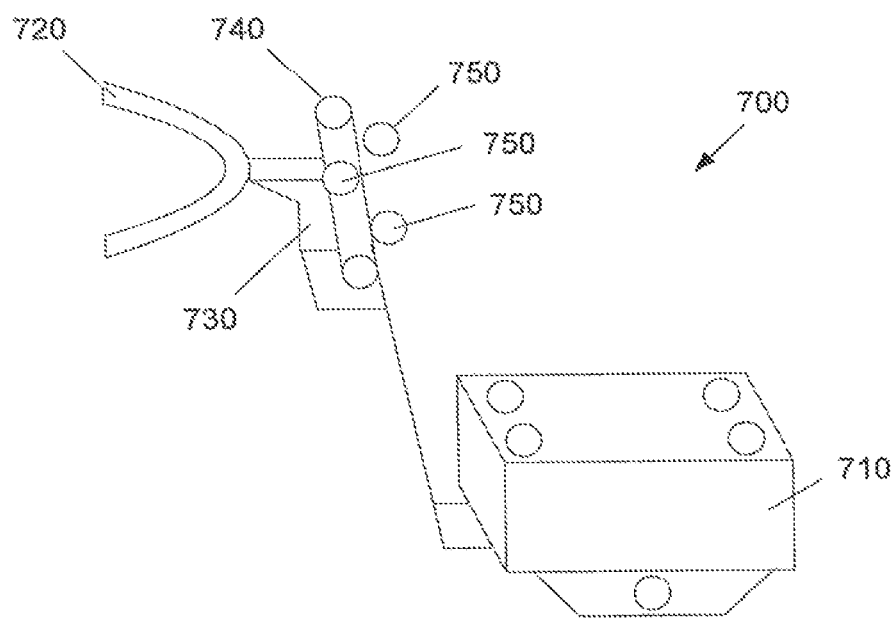
FIG. 16 illustrates a perspective view of an anatomic orientation and position recorder comprising at least one fiducial marker in accordance with an exemplary embodiment.

FIG. 16 illustrates a perspective view of an anatomic orientation and position recorder comprising at least one fiducial marker in accordance with an exemplary embodiment. The measuring device 710 may comprise a gyroscope for obtaining three-dimensional head orientation and position data comprising the X coordinate, the Y coordinate, the Z coordinate, the pitch, the roll and the yaw. Other measuring devices may be used, including but not limited to an inclinometer, without departing from the scope and spirit of the exemplary embodiment. Additionally, the measuring device may be either digital or analog without departing from the scope and spirit of the exemplary embodiment. Although the method described in this embodiment uses a bite-jig, any attachment device may be used without departing from the scope and spirit of the exemplary embodiment.

Figure 17:
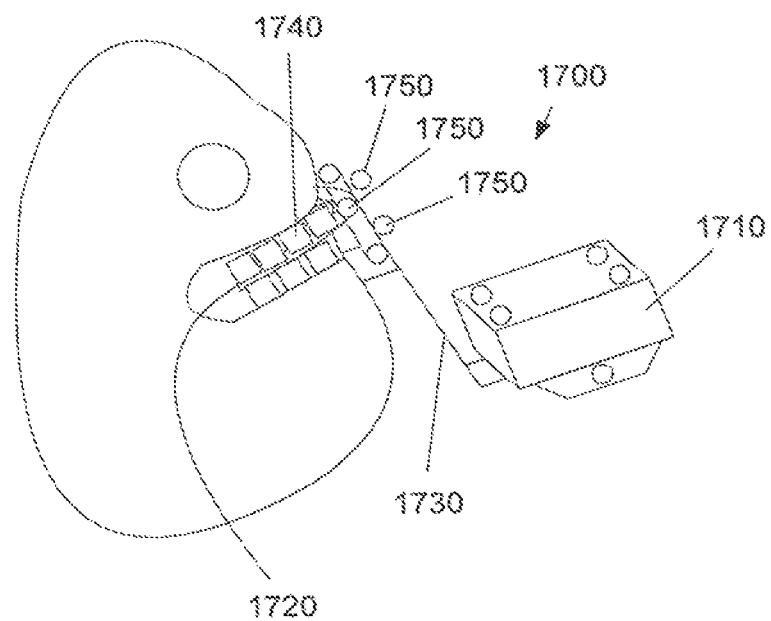
FIG. 17 illustrates a perspective view of an anatomic orientation and position recorder coupled to one or more teeth of a subject in accordance with an exemplary embodiment.

At step 1520, the bite-jig is coupled to one or more teeth of the subject. FIG. 17 illustrates a perspective view of an anatomic orientation and position recorder 1700 coupled to the one or more teeth 1740 of a subject in accordance with an exemplary embodiment. FIG. 17 shows the anatomic orientation and position recorder 1700 comprising a bite-jig 1720, a gyroscope 1710, a connector 1730 coupling the gyroscope 1210 to the bite-jig 1220 and at least one fiducial marker 1750 coupled to the connector 1730. Although this embodiment uses at least one fiducial marker for determining the orientation and position of an anatomic part, at least one surface marker, including but not limited to surface topography, may be used in lieu of or in addition to the at least one fiducial marker without departing from the scope and spirit of the exemplary embodiment.

At step 1530, the subject's head is oriented to the desired head orientation and position. This desired head orientation and position may be the natural head orientation and position or any other desired head orientation and position.

At step 1540, the desired head orientation and position is recorded in a computer using the X coordinate, the Y coordinate, the Z coordinate, the pitch, roll and yaw of the measuring device. The gyroscope measures one or more head orientation and position data 320 comprising the X coordinate, the Y coordinate, the Z coordinate, the pitch, the roll and the yaw of the measuring device as it rotates about. The distances and the angles from the measuring device to the at least one fiducial marker are constant and predetermined. The one or more head orientation and position data 320 may be recorded and stored within the database. Although this embodiment uses at least one fiducial marker for measuring the distances and angles, at least one surface marker may be used in lieu of or in addition to the at least one fiducial marker without departing from the scope and spirit of the exemplary embodiment.

At step 1550, a computerized model of the anatomic orientation and position recorder is generated. The computerized model of the anatomic orientation and position recorder 330 may be a substantially exact computer-generated representation of the anatomic orientation and position recorder. The computerized model of the anatomic orientation and position recorder 330 may be scanned into the database or may be manually recreated within the anatomic orientation and position detector system and stored within the database.

At step 1560, the head is scanned, wherein the bite-jig is coupled to the one or more teeth and wherein the head is oriented in a second orientation and position. The scanner may comprise a CT scanner. The CT scanner may scan the subject's head and the anatomic orientation and position recorder, wherein the anatomic orientation and position recorder 1700 is coupled to the subject 160. The resulting head scan 340 may be displayed on the display and/or stored within the database.

At step 1570, a three-dimensional representation of the 3D facial skeleton of the subject comprising the at least one fiducial marker is created. This three-dimensional representation of the 3D facial skeleton 345 is generated from the head scan 340 of step 1360. The 3D facial skeleton 345 may be stored within the database. Although this embodiment creates a three-dimensional representation of the 3D facial skeleton of the subject comprising the at least one fiducial marker, at least one surface marker may be used in lieu of or in addition to the at least one fiducial marker without departing from the scope and spirit of the exemplary embodiment.

At step 1580, the computerized model of the anatomic orientation and position recorder is coupled to the three-dimensional representation of the 3D facial skeleton. In one embodiment, the fiducial markers are used to couple the two images. A coupled image 350 results therefrom, wherein the user may manipulate either of the two images independently of one another. This coupled image 350 may be stored within the database. Although this embodiment uses the at least one fiducial marker to couple the two images, at least one surface marker may be used in lieu of or in addition to the at least one fiducial marker without departing from the scope and spirit of the exemplary embodiment.

At step 1590, the three-dimensional representation of the 3D facial skeleton is reoriented to the desired head orientation and position. The one or more head orientation and position data 320 is used in conjunction with the coupled image 350 to generate the re-oriented 3D facial skeleton image 360. The 3D facial skeleton 345 within the coupled image 350 is reoriented to the desired orientation and position resulting in the re-oriented 3D facial skeleton image 360.

FIG. 18 illustrates a flowchart of a method 1800 for performing surgery on a subject using a head CT scan that has been reoriented to a desired head orientation and position in accordance with an exemplary embodiment. At step 1810 one or more head orientation and position data for the orientation of the head of a subject is obtained using an anatomic orientation and position recorder, wherein the head is oriented in a desired head orientation and position. Exemplary anatomic orientation and position recorders have been previously described above. At step 1820 a computerized model of the anatomic orientation and position recorder is generated. At step 1830 the head of the subject is scanned using a CT scanner, wherein the head is oriented in a second orientation and position. At step 1840 a three-dimensional representation of the 3D facial skeleton of the subject is created. At step 1850 the three-dimensional representation of the 3D facial skeleton is reoriented to the desired head orientation and position. At step 1860 a surgery is simulated to determine the post-surgery outcome. At step 1870 the surgery is performed. In performing the surgery, the subject is first placed in the desired orientation and position and then the surgery is performed on the subject.

FIG. 19 illustrates a flowchart of a method 1900 for radiation planning on a subject. At step 1910, the subject is virtually oriented and positioned into a desired orientation and position in a computer. At step 1920, radiation treatment planning is performed on the virtually oriented and positioned subject. At step 1930, the desired orientation and position of the virtual subject is recorded. At step 1940, the subject is oriented and positioned in the desired orientation and position during actual treatment. At step 1950, the treatment is performed on the subject. Although this embodiment illustrates radiation treatment, any type of treatment that requires a subject to be in a particular orientation and position may be performed, without departing from the scope and spirit of the exemplary embodiment.

In an alternative embodiment, a user may create a representation of a subject and manipulate the representation to determine a desired orientation and position. This representation may be a three-dimensional model or an image on a display. The desired orientation and position may, but is not limited to, be an orientation and position for facilitating a medical treatment. Once the desired orientation and position is obtained from the representation, the user may orient the subject itself, using an anatomic orientation and position recorder, to the desired orientation and position and perform the medical treatment. Although this embodiment determines the desired orientation and position on the representation which then allows the subject to be placed in the desired orientation and position for a medical treatment, alternative purposes, other than facilitating a medical treatment, may be found without departing from the scope and spirit of the exemplary embodiment.

Although the invention has been described with reference to specific embodiments, these descriptions are not meant to be construed in a limiting sense. Various modifications of the disclosed embodiments, as well as alternative embodiments of the invention will become apparent to persons skilled in the art upon reference to the description of the invention. It should be appreciated by those skilled in the art that the conception and the specific embodiments disclosed may be readily utilized as a basis for modifying or designing other structures for carrying out the same purposes of the invention. It should also be realized by those skilled in the art that such equivalent constructions do not depart from the spirit and scope of the invention as set forth in the appended claims. It is therefore, contemplated that the claims will cover any such modifications or embodiments that fall within the scope of the invention. All of the compositions and methods disclosed and claimed herein can be made and executed without undue experimentation in light of the present disclosure. While the systems, apparatuses, and methods of this invention have been described in terms of preferred embodiments, it will be apparent to those of skill in the art that variations may be applied to the systems, apparatuses, and methods and in the steps or in the sequence of steps of the method described herein without departing from the concept, spirit and scope of the invention. More specifically, it will be apparent that certain agents, which are chemically and/or physiologically related, may be substituted for one or more of the agents described herein, while achieving the same or similar results. All such similar substitutes and modifications apparent to those skilled in the art are deemed to be within the spirit, scope and concept of the invention as defined by the appended claims.

What is claimed is:

1. An apparatus for recording a first anatomical position of a selected body part of a patient, comprising:
   (a) an attachment device, wherein the attachment device couples to at least one selected body part of the patient;
   (b) a measuring device, comprising a gyroscope, an inclinometer, or a combination thereof, wherein the measuring device measures the orientation of a first anatomical position of the selected body part relative to a known landmark within the body of the patient;

(c) a connector that couples the measuring device to the attachment device, and (d) at least three non-collinear fiducial markers that are operably positioned relative to the connector at predetermined fixed distances and predetermined fixed angles relative to each other to define a three-dimensional space;

wherein the measuring device is orthogonal to the three, non-collinear fiducial markers, and further wherein the orientation of the first anatomical position of the selected body part is measured three-dimensionally using pitch, yaw, and roll data obtained from the measuring device.

2. The apparatus of claim 1, wherein the first anatomical position of the selected body part comprises a natural position.

3. The apparatus of claim 1, wherein the fiducial markers comprise a CT- or an MRI-detectable material.

4. The apparatus of claim 1, wherein the measuring device is digital.

5. The apparatus of claim 1, wherein the attachment device comprises an attachment band or a jig.

6. The apparatus of claim 5, wherein the jig comprises an individualized occlusal bite registration.

7. The apparatus of claim 6, wherein the individualized occlusal bite registration comprises a radiolucent material.

8. The apparatus of claim 7, wherein the radiolucent material comprises a dental acrylic material.

9. The apparatus of claim 1, wherein the selected body part comprises one or more teeth of the patient.

10. A method for recording a desired anatomical position of a first part of a patient's body in three-dimensions, comprising:

(a) obtaining a position recorder comprising: an attachment device that comprises three, non-collinear fiducial markers, operably positioned and coupled orthogonally or perpendicularly to a measuring device that comprises a gyroscope, an inclinometer, or a combination thereof, (b) coupling the position recorder to the first part of the patient's body at one or more defined locations;

(c) orienting the patient's body to a desired anatomical position of a first part thereof; and (d) recording the selected first part of the patient's body in three-dimensions, wherein a frame of reference of the measuring device is aligned with a reference frame that is defined by the orientation and placement of the three, non-collinear fiducial markers.

* * * * *